(12) United States Patent
Kammerzell et al.

(10) Patent No.: US 7,594,933 B2
(45) Date of Patent: Sep. 29, 2009

(54) METHOD AND APPARATUS FOR POSITIONING A BONE PROSTHESIS USING A LOCALIZATION SYSTEM

(75) Inventors: Sergej Kammerzell, Engen (DE); Uwe Bader, Tuttlingen (DE); Benoit Mollard, Echirolles (FR)

(73) Assignee: Aesculap AG (DE)

( * ) Notice: Subject to any disclaimer, the term of this patent is extended or adjusted under 35 U.S.C. 154(b) by 388 days.

(21) Appl. No.: 11/463,268

(22) Filed: Aug. 8, 2006

(65) Prior Publication Data
US 2008/0051910 A1  Feb. 28, 2008

(51) Int. Cl.
*A61F 2/32* (2006.01)
(52) U.S. Cl. .................... 623/22.15; 600/424
(58) Field of Classification Search ............ 623/22.12
See application file for complete search history.

(56) References Cited

U.S. PATENT DOCUMENTS

| | | | |
|---|---|---|---|
| 6,711,431 B2 | 3/2004 | Sarin et al. | |
| 6,991,655 B2 | 1/2006 | Iversen | |
| 7,001,346 B2 | 2/2006 | White | |
| 2003/0105470 A1* | 6/2003 | White | 606/102 |
| 2004/0092944 A1 | 5/2004 | Penenberg | |
| 2004/0230199 A1 | 11/2004 | Jansen et al. | |
| 2005/0065617 A1 | 3/2005 | Moctezuma de la Barrera et al. | |

FOREIGN PATENT DOCUMENTS

| WO | 2005023110 A1 | 3/2005 |
|---|---|---|
| WO | 2006079211 A1 | 8/2006 |
| WO | PCT/EP2007/058099 | 12/2007 |

* cited by examiner

*Primary Examiner*—Corrine M McDermott
*Assistant Examiner*—Rebecca Straszheim
(74) *Attorney, Agent, or Firm*—RatnerPrestia

(57) ABSTRACT

Methods and apparatus using a surgical navigation system during hip joint replacement surgery without separately affixing a marker to the femur. The navigation system acquires the center of rotation of the hip joint as well as at least one point on the femur in the pelvic frame of reference. From these two points, the navigation system calculates the position and length of a first line between the center of rotation of the hip joint and the point on the femur. A prosthetic cup is implanted and its center of rotation is recorded. A tool for forming the bore within which the stem of the femoral implant component will be placed is tracked by the navigation system. The navigation system calculates the position and length of a first line between the center of rotation of the prosthetic cup and the re-palpated first point. The surgical navigation system uses this information to calculate and display to the surgeon relevant information about the surgery.

37 Claims, 8 Drawing Sheets

METHOD AND APPARATUS FOR POSITIONING A BONE PROSTHESIS USING A LOCALIZATION SYSTEM

BACKGROUND OF THE INVENTION

The present invention relates to surgical navigation systems, sometimes called localization devices. More particularly, the present invention relates to methods and apparatus for positioning a bone prosthesis during orthopedic surgery using a surgical navigation system.

Many different types of surgical navigation systems are known, including surgical navigation systems that rely on optical, electromagnetic, mechanical, ultrasonic, and gyroscopic position and/or orientation sensing techniques and apparatus. Optical-, electromagnetic-, mechanical-, and ultrasonic-based surgical navigation systems are well known at this time. Gyroscopic-based surgical navigation systems are, perhaps, not as well established. Gyroscopic systems use inertial sensors. In gyroscopic systems, each marker comprises one or more gyroscopes. If six gyroscopic sensors are incorporated on a rigid body marker, namely, three sensors for detecting force and/or acceleration in linear directions and three sensors for determining rotational forces or acceleration, a marker can be tracked in all six degrees of freedom. Note that gyroscopic sensors do not provide information as to position per se, but to acceleration or movement. The positions and/or orientations of such sensors are not determined directly in a coordinate system, but are calculated from changes in position and orientation.

In an exemplary infrared, optical surgical navigation system 100 such as illustrated in FIG. 1, at least two sensors 114a, 114b (e.g., infrared cameras) mounted in a housing 128 are used to detect a plurality of markers 116a, 116b, 116c, 116d, 116e that can be mounted on the patient's bones 105a, 105b and/or on surgical tools 124. More particularly, the cameras 114a, 114b are coupled to a computer 112 that analyzes the images obtained by the cameras and detects the positions and orientations of the various bones and/or tools bearing the markers during the surgery and calculates and displays useful information for performing the surgery to the surgeon on a monitor 122. The computer system may be provided in a portable cart 108 and may include a memory 110 for storing data, a keyboard 120, and/or foot pedals 118 for entering data. Typically two or more of the markers 116a-116e are used simultaneously. One such surgical navigation system is the OrthoPilot available from Aesculap, Inc. of Center Valley, Pa., USA.

Each marker 116 comprises a base with a mounting mechanism 217 on one end for mounting to a complementary mounting mechanism 201 on a piece of medical equipment such as surgical pointer 124, a bone screw, or a cutting jig. Extending from the other end of the base are at least three infrared LED transmitters 208. Alternately, instead of transmitters, the system could utilize markers 116a bearing infrared reflectors 208a, as shown in FIG. 2B, which illustrates an exemplary marker 116a of the reflector type. When using reflectors, the surgical navigation system includes an infrared light source 107 directed towards the surgical field so that the reflectors 208 will reflect infrared light back to the two cameras 114a, 114b. With at least three transmitters 208 (or reflectors 208a) per marker and at least two cameras, sufficient information is available to the computer to determine the exact position and orientation of each marker 116 (or 116a) in all six degrees of freedom (e.g., x, y, z, coordinates and roll pitch and yaw angles).

The mounting mechanism at the end of the base of the marker is designed to mate with a complementary mounting mechanism on the surgical instrument in only one position and orientation. The computer is preprogrammed with information relating to the position of the operational portion of the medical instrument relative to the position of the marker when mounted on it. In this manner, by detecting the position and orientation of the marker, the computer will also know the position and orientation of the medical instrument and its operational portion. For instance, the medical instrument may be the pointer 124 shown in FIG. 1 having a tip 124a, the exact position of which is known relative to the marker 116a.

In most surgical navigation procedures, it is necessary to discern the markers 116 or 116a from each other. This can be done in several different ways. If LED transmitters are used, each transmitter 208 can be timed to emit light only during a specific time interval that the computer knows is the time interval assigned to that particular transmitter on that particular marker. The LEDs are illuminated in sequence at a very high rate so that the computer has virtually continuous information as to the exact location of every LED. Alternately, when using reflectors, each marker 116a may have its three or more reflectors 208a positioned in slightly different relative positions to each other so that the computer can discern which marker it is observing by determining the geometric relationship between the three or more reflectors 208a on the marker 116a.

The markers 116 are fixedly mounted on bones 105 (via bone screws) and or medical instruments 124 (FIG. 1) or 202 (FIG. 2A) positioned within the field of view of the cameras 114a, 114b so that the computer 112 can track the location and orientation of those bones and/or medical instruments. The computer will then generate useful information to help the surgeon determine appropriate locations or alignments for prosthetic implants, cutting jigs, and the like and display it in a display 123 on the monitor 122.

One known use for surgical navigation systems is in total hip joint replacement surgery. In total hip joint replacement surgery, for instance, the patient's hip joint is replaced with prosthetic components including a prosthetic cup (essentially a ball socket) mounted on the pelvis in the reamed acetabulum and a prosthetic femoral component, comprising a ball shaped head mounted on a stem. The stem is inserted in a prepared channel along the femoral canal. The ball will fit in the cup to form the new, prosthetic hip joint.

Presently, there are several surgical navigation systems on the market that offer a total hip replacement module. Depending on the surgical navigation system and software, the system is used to assist in the positioning of only the pelvic component, i.e., the cup, while the femoral component is positioned manually or the surgical navigation system is used to assist in the positioning of both the cup and the femoral component.

Some of the most important positioning parameters for hip joint replacement are (1) lengthening/shortening of the leg (also referred to as cranialization/caudalization), (2) medialization/lateralization of the leg and/or femoral offset, and (3) range of motion.

Lengthening/shortening refers to the change, if any, in the length of the patient's leg after the prosthetic hip joint has been installed. Usually, it is desirable for both of the patient's legs to be of equal length after the surgery. Often, this means that there should be no lengthening or shortening. However, often the legs are not of equal length before the surgery and, thus, it may be desirable to increase or decrease the patient's leg length.

There is no clear agreement in the profession as to an exact definition of either medialization/lateralization or femoral offset. However, generally they are measurements indicative of the distance that the muscles that attach to the pelvis must traverse. Femoral offset generally is a feature of the femur itself, whereas medialization/lateralization is a feature of the entire joint, including the pelvis and the femur. For purposes of this discussion, we shall consider femoral offset to be the shortest distance between the femoral mechanical axis (i.e., the line connecting the center of rotation of the hip joint to the center of rotation of the knee joint) and the point where the femoral canal and the femoral neck cross each other. The offset distance typically is in the direction of the femoral neck, which typically is at an angle of about 15 degrees to the frontal plane when viewed in a horizontal plane (i.e., a plane perpendicular to the cranial caudal direction). For purposes of this discussion, medialization/lateralization is the sum of (1) the change in position of the center of rotation of the hip joint in the medial/lateral plane (by virtue of reaming of the acetabulum and implantation of a prosthetic cup, for instance) and (2) the change in femoral offset (by virtue of the removal of the top of the femur and implantation of a prosthetic stem and ball, for instance).

If the final configuration of the joint and bones results in an overall medialization (As compared to the original configuration), the muscles that attach to the pelvis will have reduced tension and a reduced lever arm, leading to weakness in the leg. On the other hand, if the final configuration of the joint and bones results in an overall lateralization, the lever arm and tension is increased, which generally dictates greater patient leg strength as well as longer life of the prostheses.

Finally, range of motion refers to the angle to which the femur can be bent before the stem of the femoral implant impinges on the pelvis. Of course, it is desirable for the patient to have about the same range of motion after the surgery as before.

In the surgical navigation systems that assist surgeons in the placement of both the pelvic implant and the femoral implant, a marker that can be tracked by the surgical navigation system is mounted to each of the pelvis and the femur. Various anatomical landmarks on the pelvis are palpated and recorded in the pelvic frame of reference (i.e., relative to the pelvic marker). Likewise, various anatomical landmarks on the femur are recorded in the femoral frame of reference (ie., relative to the femoral marker). Furthermore, the relationship of the pelvic marker and the femoral marker are registered to one another so that the pelvic frame of reference and the femoral frame of reference can be registered to one another in the overall frame of reference of the surgical navigation system.

During cup navigation, the surgical navigation system tracks the pelvic marker as well as a second marker mounted on a surgical instrument, such as a reamer for reaming the acetabulum for accepting the prosthetic cup or to the cup implant itself, either directly or via an impacter rigidly coupled to the cup. The surgical navigation system is programmed to determine the position and orientation of the cup relative to the various anatomical landmarks on the pelvis. The orientation and position of the surgical instrument and/or implant relative to the pelvis is tracked and recorded by the surgical navigation system. The surgical navigation system will display on the monitor various data to help the surgeon affix the cup in the proper position and orientation relative to both the pelvis and the femur. Such relevant information may include the position of the center of rotation of the cup, and the angular orientation of the cup in both anteversion and inclination. This can be done, for instance, by tracking the reamer, and particularly, its final position and orientation at the end of the reaming, since the position and orientation of the reamer at the end of the reaming process largely dictates the position and orientation that the cup implant will take when implanted.

It typically will also be desirable to subsequently track the cup directly during its implantation (via a marker mounted to the cup either directly or via the impacter tool that usually is rigidly affixed to the cup during its implantation). Specifically, while the reaming operation essentially dictates the final coordinate position of the cup and cannot be changed during cup implantation, the orientation of the cup actually can be affected during implantation of the cup. Therefore, it is advisable to also track the cup during implantation and display at least its anteversion and inclination angles, if not its coordinate position.

Similarly, during navigation of the femoral implant, the surgical navigation system tracks the femoral marker and a second marker attached to a surgical instrument, such as a rasp for creating the channel within which the femoral component will be implanted and/or the stem portion of the femoral implant itself. The pelvis does not need to be tracked. However, since the surgeon has already implanted the cup in the pelvis and the system has recorded the position of the cup, the surgical navigation system also may track the pelvis (via the pelvic marker) during the femoral implantation stage of the procedure. The surgical navigation system can display to the surgeon relevant information for properly orienting and positioning the femoral implant. This information may include not only the parameters determined by the positional relationship of the femoral implant to the femur, but also the global changes of the hip joint based on the position and orientation of the cup implant and femoral implant with respect to various landmarks on the pelvis and/or femur. This information may include, for instance, anteversion and inclination angles for the joint, leg lengthening/shortening, leg medialization/lateralization, and range of motion.

In order for conventional surgical navigation systems to provide the navigational assistance with respect to the placement of the femoral implant as outlined above, a marker must be mounted on the femur. Placement of a marker on the femur is time-consuming. Additionally, the need to place a marker on the femur requires either an additional incision during the surgical procedure or additional space within the surgical approach and, therefore, a bigger skin cut in order to accommodate it. This is contradictory to the minimally invasive approach desired in modern orthopedic surgical procedures.

Accordingly, it is an object of the present invention to provide an improved method and apparatus for surgical navigation.

It is another object of the present invention to provide an improved method and apparatus for performing hip joint replacement surgery using a surgical navigation system.

It is a further object of the present invention to provide an improved method and apparatus for performing hip joint replacement surgery using a surgical navigation system that eliminates the need to affix a marker to the femur.

SUMMARY OF THE INVENTION

The present invention provides methods and apparatus using a surgical navigation system for assistance in performing joint replacement surgery, particularly hip joint replacement surgery. More particularly, the invention permits the use of a surgical navigation system to assist in the positioning of the femoral component of a prosthetic hip without the need to affix a femoral marker. A surgical navigation system is used to acquire, in the pelvic frame of reference, the pre-operative center of rotation of the hip joint and at least one point relatively fixed with respect to the femur, preferably, on or near the femoral mechanical axis. This point may be a point on the patella (which is a separate bone from the femur but which is relatively fixed with respect to the femur and which can be palpated over the skin). From these two points, the navigation system calculates the position and length of a line between the center of rotation of the hip joint and the acquired point on the femur, which is roughly the femoral mechanical axis.

Optionally, one may palpate a second point on the femur that is not on the line between the center of rotation of the hip joint and the first palpated point (e.g., the point on the patella). This second femoral point may be a point on the greater trochanter, which can be palpated through the femoral cut that is typically made in connection with hip replacement surgery. The system can calculate the position and length of a second line perpendicular to the first line and that runs from the first line to the second palpated point on the femur (e.g., the trochanter). Additional points on the femur also may be palpated and recorded by the navigation system and additional relationships calculated.

The prosthetic cup is implanted in the acetabulum and its center of rotation is recorded by the surgical navigation system. Next, a tool such as a rasp is used to form and define a channel in the femur within which the stem of the femoral implant component will be placed. This tool is tracked by the surgical navigation system. While the tool is rigidly fixed to the femur in the final position that defines the channel within which the femoral implant will be positioned and tracked by the navigation system, the surgeon re-palpates the same femoral point(s) (e.g., patella and/or trochanter) that were previously palpated.

The position of the rasp can be converted directly into a center of rotation of the prosthetic femoral head when the femoral prosthetic component is eventually implanted into the channel. Thus, from the collected data, the surgical navigation system can calculate the position and length of the line between the center of rotation of the prosthetic femoral head and the re-palpated first femoral point. If a second point on the femur was palpated (e.g., the trochanter), the surgical navigation system also calculates the position and length of the perpendicular line between the first line and the second point. Since the navigation system also had recorded the center of rotation of the implanted cup in the pelvis, it knows exactly where the center of rotation of the prosthetic femoral head will be within the pelvic frame of reference when the joint is reassembled.

The surgical navigation system uses this information to calculate and display to the surgeon relevant information about the surgery. For instance, the change in position of the center of rotation of the prosthetic cup relative to the original center of rotation of the native acetabulum combined with the change in length of the line between the center of rotation of the original acetabulum and the palpated patella point, on the one hand, and the length of the line between the new center of rotation of the prosthetic femoral head and the re-palpated patella point gives the change in the patient's leg length. Likewise, the difference in the length of the perpendicular line between the trochanter (as first palpated) and the line between the center of rotation of the original acetabulum and the palpated patella point, on the one hand, and the trochanter point (as re-palpated) and the line between the new center of rotation of the prosthetic femoral head and the re-palpated patella point, on the other hand, gives the medialization/lateralization of the joint.

DETAILED DESCRIPTION OF THE INVENTION

A description of a suitable optical localization device (surgical navigation system) for use in connection with the present invention is found in U.S. Pat. No. 6,385,475 to Cinquin et al., which is incorporated herein by reference. The invention will be described in connection with an infrared optical surgical navigation system such as disclosed in this patent. However, it should be understood that this is merely exemplary and that the present invention can be used in connection with many types of surgical navigation systems, including, but not limited to, surgical navigation systems that utilize optical, gyroscopic, electromagnetic, mechanical, and ultrasonic position/orientation sensing techniques.

Below will be described the significant steps in an exemplary hip joint replacement surgical procedure utilizing concepts, methods, and apparatus in accordance with the present invention. It should be understood that the description is merely exemplary and that the invention is not limited either to the particular embodiment described herein or the particular exemplary surgical navigation system in connection with which is described in these exemplary embodiments.

The leg should be placed in approximately the same amount of knee flexure for the acquisition phase as well as the implantation phase in order to maximize accuracy. Preferably, the leg is slightly flexed during the entire surgery to a knee flexure of about 30° to 90°.

In the first part, a pelvic frame of reference should be established. Accordingly, a marker is rigidly affixed to the pelvis, such as by a cortical screw. This marker may be mounted through the main surgical approach or, alternately, it may be mounted to the pelvic crest through a separate incision.

Figure 1:
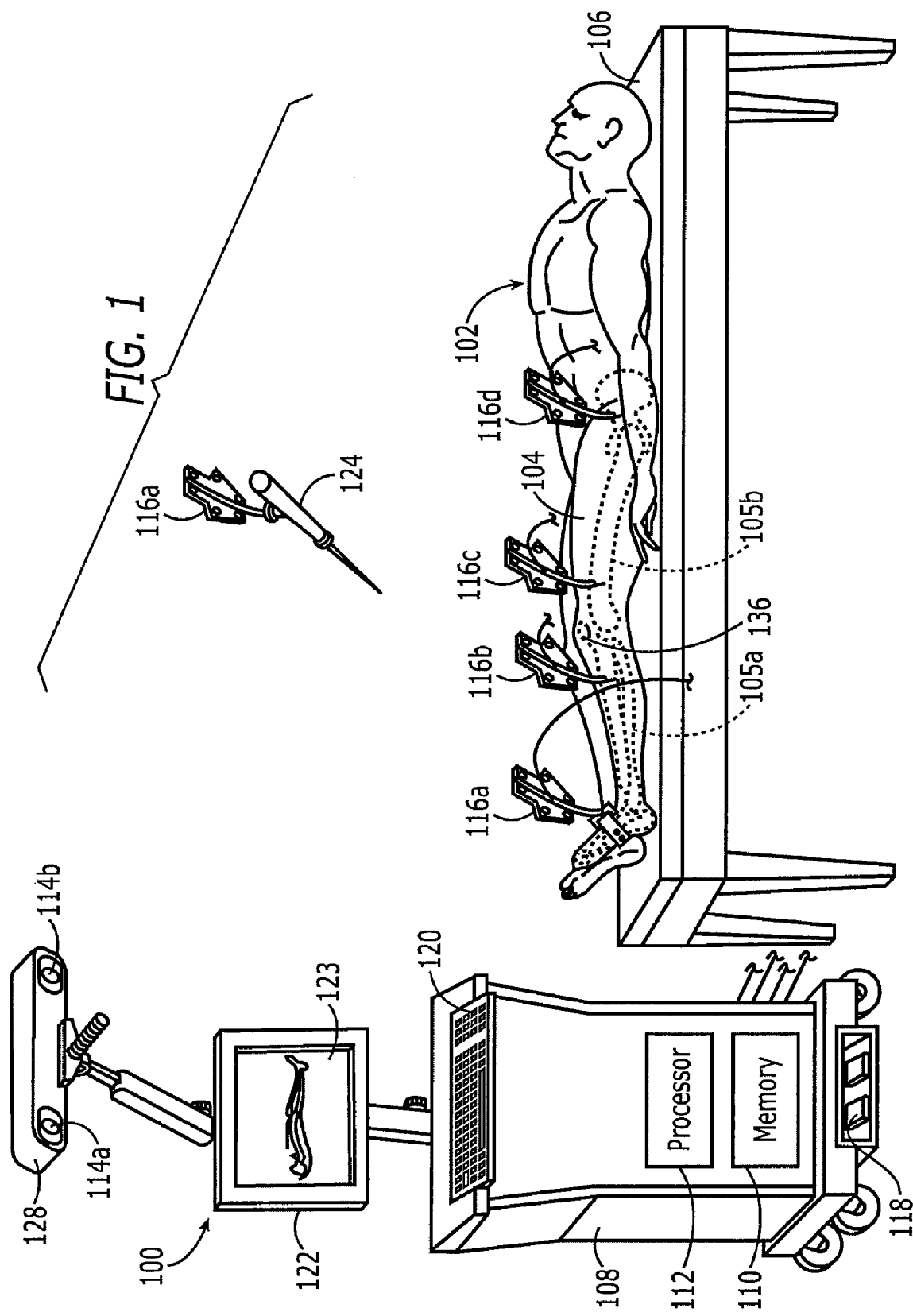
FIG. 1 is an illustration of a surgical navigation system being used for orthopedic surgery in accordance with the prior art.
Figure 2:
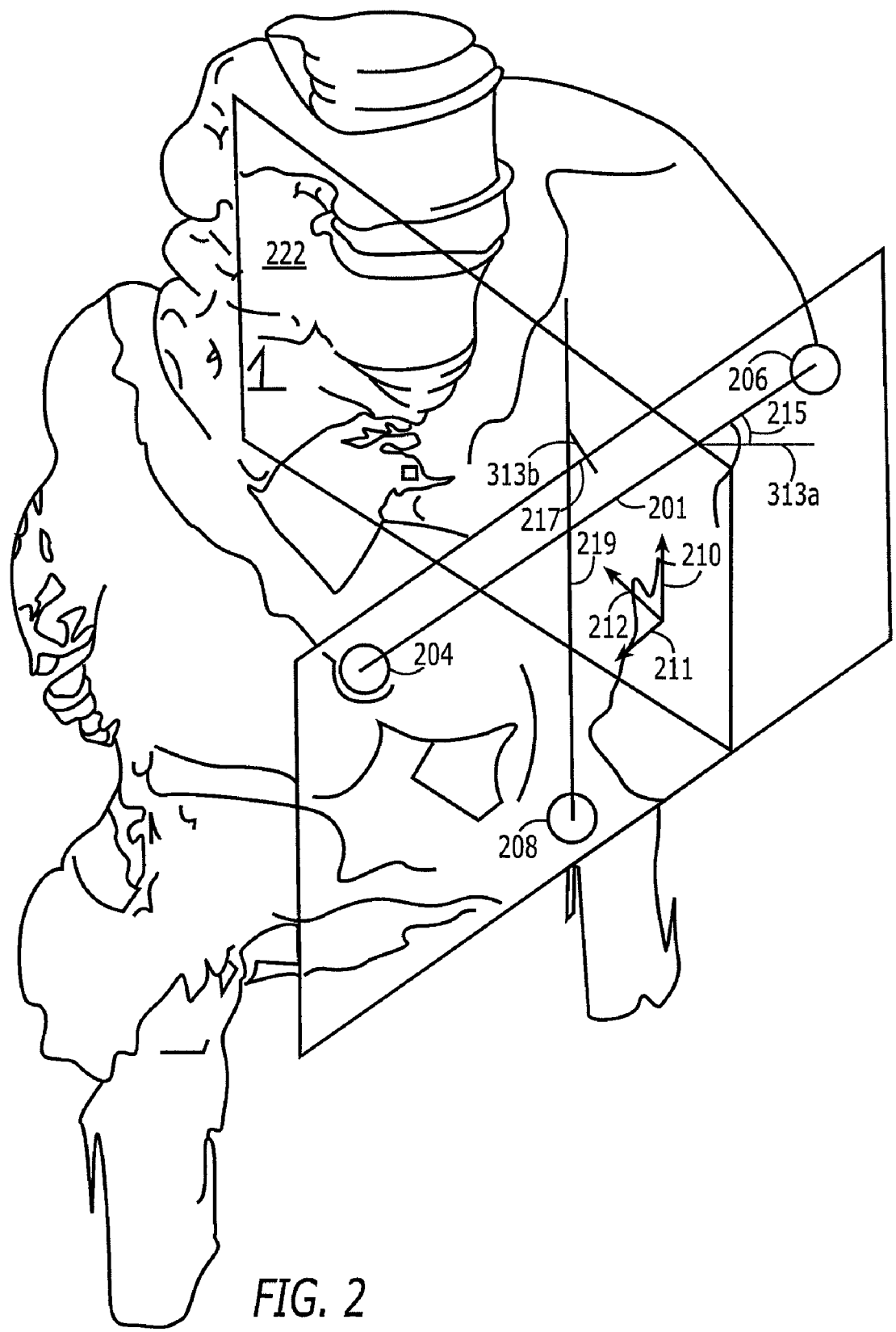
FIG. 2 is a drawing of a pelvis illustrating the anterior pelvic plane and other reference landmarks on the pelvis.

Anatomical landmarks on the pelvis should be palpated and recorded relative to the pelvic marker by the navigation system in order to define a pelvic frame of reference with respect to the tracked marker. In at least one embodiment, the pelvic frame of reference can be the anterior pelvic plane, as illustrated at 202 in FIG. 2. The anterior pelvic plane 202 can be determined by palpating three non-coaxial points on the pelvis, for instance, the left and right iliac spine anterior superior points 204, 206 and the symphysis pubis 208, and calculating the plane defined by those three points.

In a preferred embodiment of the invention, the navigation system uses the monitor to inform the surgeon of the steps to be performed pictorially, textually or both throughout the entire surgical procedure. Thus, for instance, in connection with palpating the three aforementioned points on the pelvis, the monitor may display a graphic representation of a pelvis with a pointer touching the anatomical landmark to be palpated at that time. Additionally, the monitor may also display a textual instruction, such as "palpate the symphysis pubis". The surgeon would palpate the point and would perform some operation, such as stepping on a pedal coupled to the computer of the navigation system, to indicate to the navigation system to record the position of the tip of the surgical pointer at that instant in time as the symphysis pubis.

Figure 3:
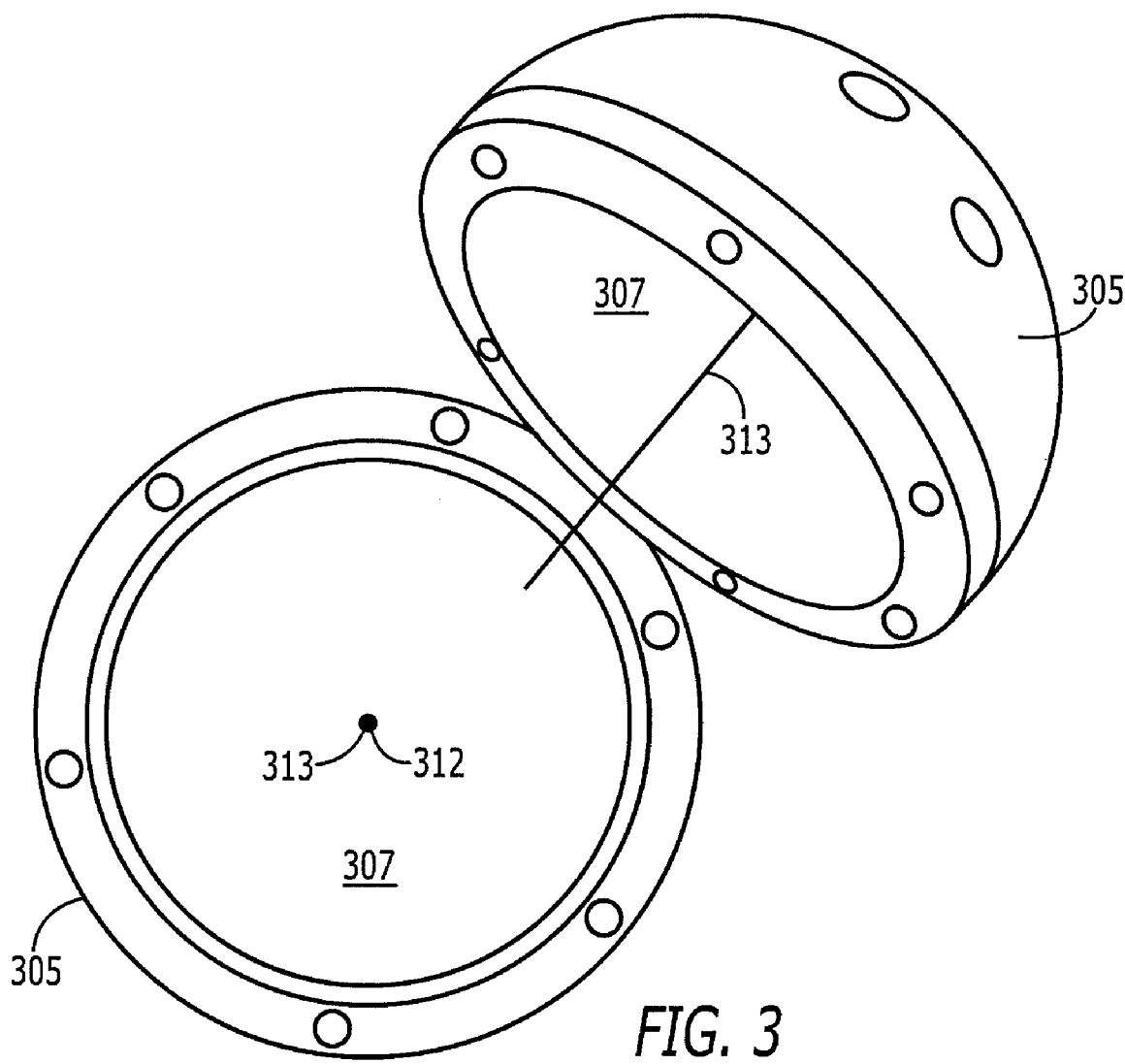
FIG. 3 is a pictorial representation of an exemplary prosthetic cup for hip replacement surgery.

Once these three points have been palpated, the navigation system calculates the position of the anterior pelvic plane in the pelvic frame of reference (i.e., as a function of the position of the pelvic marker). The anterior pelvic plane will be the reference plane for the placement of the prosthetic cup. More particularly, the line 201 between the left and right superior points 204, 206 will be used as the reference line for indicating the angle of inclination of the cup. With reference to FIG. 3, which shows a front plan view and a perspective view of an exemplary prosthetic cup 305, let us consider the diameter line 313 that extends from the geometric center 312 of the cup 305 perpendicular to the equatorial plane 307 through the center of the sphere defined by the cup to be the reference line for angular orientation of the cup. Referring back to FIG. 2, inclination is the angle 215 of the cup reference line 313 in the anterior pelvic plane 202 relative to line 211. When a projection 313a into the frontal plane of the diameter line 313 of the cup 305 is in the caudal direction 315, the cup has an inclination of 0°. When the projection into the frontal plane of radius line 313 is facing in the lateral direction 211, the cup has an inclination angle of 90°.

A second reference line 219 perpendicular to the first line 201 and running through the symphysis pubis 208 will be used as a reference for the anteversion angle of the cup. Anteversion is the angle 217 of the cup in the sagittal plane 222 about an axis running in the cranial caudal direction, e.g., line 219. When the projection 313b into the sagittal plane of the aforementioned diameter line 313 of the cup is pointing in the caudal direction 210, the cup has an anteversion angle of 0°. When the projection 313b of line 313 into the sagittal plane is running in the sagittal direction 211, the anteversion angle of the cup is 90°.

Note that, in the relevant fields, there are different definitions of anteversion and inclination depending on the context. The above operative-context definitions are merely ones of several possible definitions. For instance, Murray, D. W., The Definition and Measurement of Acetabulem Orientation, The Journal of Bone and Joint Surgery, Col. 75-B, No. 2, March 1993, p. 228, identified the more common definitions of anteversion and inclination in the anatomical, radiographic, and operative contexts. As will become clear from the discussion below, the present invention can be readily adapted to calculate anteversion and inclination in any of these contexts.

The desired inclination and anteversion angles for the prosthetic cup 305 are up to the surgeon and can vary from patient to patient. However, an inclination angle of about 45° and an anteversion angle of about 15° are typical.

Next, the navigation system instructs the surgeon to acquire desired data with respect to the femur. The surgeon should palpate at least one point associated with the femur while the navigation system records that point in the pelvic frame of reference (i.e., relative to the pelvic marker). In a preferred embodiment of the invention, this point is on or near the mechanical axis of the femur and may be one of the epicondyles or a point on the patella. Either the epicondyles or the patella can be palpated over the skin such that no surgical incision need be made to palpate the point. Although the patella is a separate bone from the femur, its position relative to the femur is substantially fixed during the surgery and therefore can be used as a femoral reference point. If the surgical navigation system will be used with respect to the navigation of the femoral component of the prosthesis hip with respect to leg lengthening/shortening, then it is sufficient to palpate only this one point.

However, if the navigation system will be used to guide the surgeon with respect to additional parameters in connection with the positioning and orientation of the femoral component of the prosthetic hip, then at least one additional point associated with the femur should be palpated.

For instance, as previously noted, the medialization/lateralization of the leg also is a significant factor in the implantation of a prosthetic hip. If the system is to assist with the medialization/lateralization also, then at least one other point should be palpated on (or substantially stationary with respect to) the femur that is not on the line between the first palpated point (e.g., the patella) and the center of rotation of the hip joint. In a preferred embodiment of the invention, this second point may be a point on the greater the trochanter, which is accessible through the femoral cut and, thus, does not require an additional or larger incision in order to be palpated.

In accordance with at least one embodiment of the invention, the surgeon will re-palpate the same points or points on (or associated with) the femur later in the surgery. Therefore, preferably, the surgeon visibly marks the point or points so that the surgeon can find those points again later. With respect to the point on the patella, it can be easily marked with a skin marker or pen. Also, camera systems are now available that can track the position of a single reflecting ball. Hence, the point may alternately be marked by such a ball mounted to the patella by adhesive over the skin. Even further, the surgeon can make an incision and mount a screw into the patella or epicondyle to facilitate the later re-palpation of the same point. The trochanter can be marked with a small bone screw, an infrared reflector marker, a light emitting marker, a gyroscopic sensor marker, an electromagnetic sensor marker, or burned with a hot knife or high-frequency burning implement in order to leave a mark.

Note that there is no femoral bone marker mounted to the femur and that these points are recorded by the navigation system in the pelvic frame of reference. Since the femur is movable relative to the pelvis, if more than one point on the femur is palpated, those points should be palpated in such a way that either the femur is not moved between the time that the two or more points are palpated or the two or more points are palpated simultaneously with two or more separate surgical pointers and recorded by the navigation system simultaneously.

Next, the joint is disassembled by removing the femoral head from the acetabulum. First, the surgeon palpates a point on the surface of the native acetabulum that can be used as a reference point on the surface of the native acetabulum from which the navigation system references (and displays to the surgeon) the depth of the reamer surface during reaming of the acetabulum. To increase the accuracy of this calculation, the navigation system can instruct the surgeon to palpate and record more than one point on the surface of the acetabulum and the navigation system can choose the most superficial of these points for calculating the relative reamer depth.

Next, the surgeon chooses a trial cup that best fits the native acetabulum and mounts it to an impacter (essentially a rod that screws into a screw hole in the center of the trial cup) or other rigid instrument and mounts a marker to the impacter. The surgeon then places the trial cup in the native acetabulum in a position and orientation that best reflects the position and orientation of the native acetabulum while the systems records this position and orientation. The navigation system then calculates the center of rotation of the test cup (which presumably defines the center of rotation of the native acetabulum) as well as the angles of inclination and onteversion from this data.

Other techniques also are available for determining the center of rotation of the native acetabulum and can be implemented in the present invention. For instance, some systems ask the surgeon to palpate a plurality of points on the native acetabulum and then calculate the sphere that best matches those points. The system then uses the center of that sphere as the center of rotation of the native acetabulum. The precise technique by which the center of rotation of the native acetabulum is not significant, as long as it is determined.

While the joint was still intact, the center of rotation of the femoral head was, by definition, the same point as the center of rotation of the acetabulum. Thus, by determining the center of rotation of the acetabulum as discussed above, the system also has, by definition, determined the center of rotation of the femoral head when the joint was still assembled. Since the palpated femoral point(s) were recorded in the pelvic frame of reference while the joint was still assembled, those femoral points were recorded in the pelvic frame of reference while the center of rotation of the femoral head had a known, fixed relationship to the pelvic frame of reference, even though that position was not yet determined in the pelvic frame of reference at that time. Specifically, the position of the center of rotation of the femoral head was the same as the center of rotation of the acetabulum. Thus, even though the position of the center of rotation of the femoral head was not recorded simultaneously with the recording of the other femoral landmark(s) (or recorded sequentially with the femur remaining stationary), once the center of rotation of the acetabulum is later determined as just described above, it is known that this point also was the position of the center of rotation of the femoral head as the time the other femoral landmark(s) were recorded. Hence, once the navigation system determines the center of rotation of the acetabulum, the navigation system also knows the position of all of three femoral landmarks (e.g., the center of rotation of the femoral head, the patella, and the trochanter) relative to each other in the pelvic frame of reference, even though the third femoral landmark (the center of rotation of the femoral head) was never palpated.

If it is desired to determine and display to the surgeon additional information, then additional points on the femur and/or pelvis can be palpated and recorded by the system, such as the minor trochanter, for use in calculating and/or displaying any such additional information.

The positions of the center of rotation of the femoral head, the patella, and the trochanter relative to each other provide sufficient data for the navigation system to determine the pre-surgical length of the femur and medial/lateral position of the femur relative to the pelvis, which will later be compared to similar post-surgical data to determine and display to the surgeon leg lengthening/shortening data and medialization/lateralization data.

Specifically, the aforementioned three points define a triangle. Particularly, with reference to FIG. 4, P represents the palpated patella point, A represents the center of rotation of the femoral head, and T represents the palpated point on the greater trochanter. The position of the pelvic marker 404 is represented as R. The y direction is the medial to lateral direction and the z direction is the caudal to cranial direction in FIG. 4. The x direction (not shown, but in and out of the page in FIG. 4) is the sagittal direction.

Figure 4:
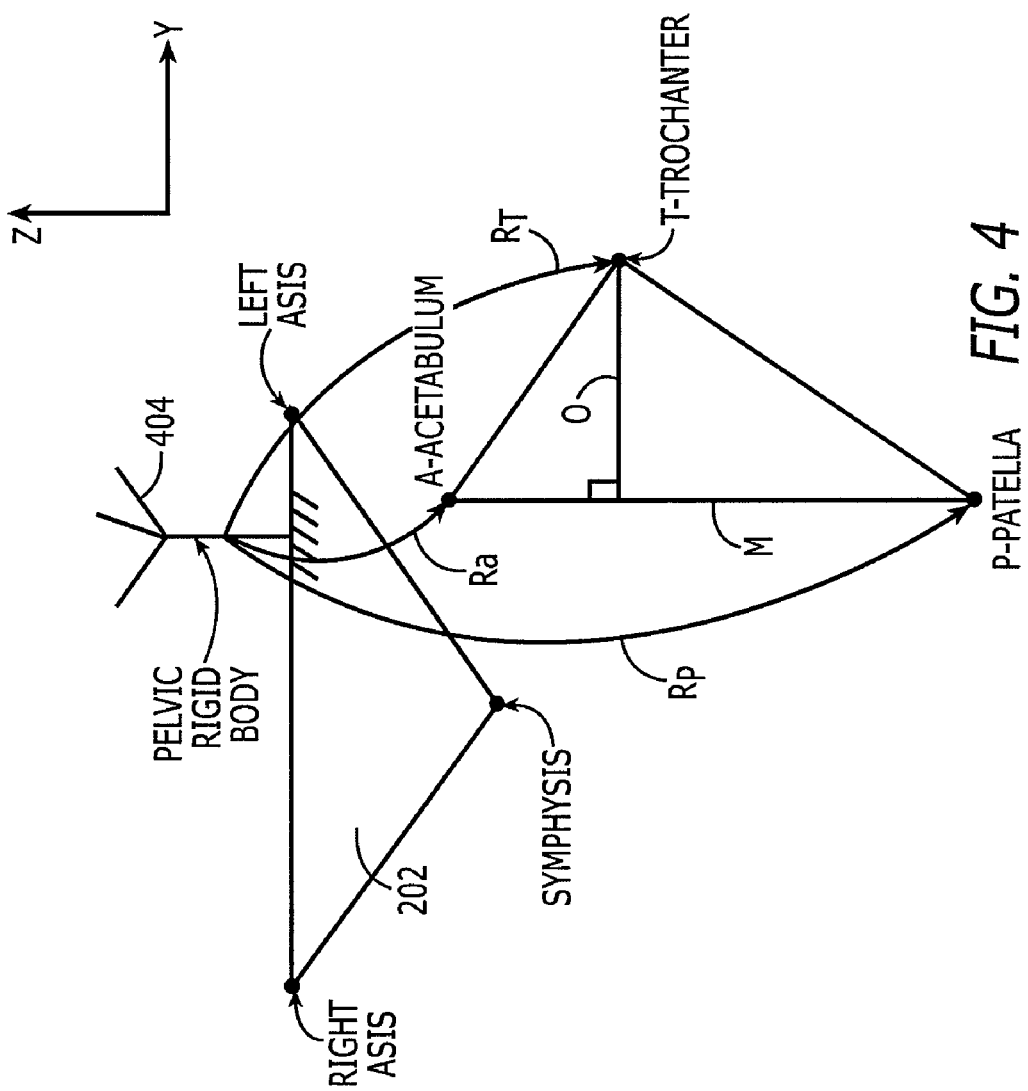
FIG. 4 is a drawing illustrating a first set of relevant landmarks and measurements in the pelvic frame of reference in accordance with an embodiment of the present invention.

The absolute positions of points A, P, and T, of course, are not actually known; only the positions of these points relative to the pelvic marker R. The x, y, z coordinates of points A, P, and T relative to the position R of the pelvic marker are represented in FIG. 4 as $R_A$, $R_P$, and $R_T$, respectively. However, in order to simplify the discussion, we will refer to the points A, P, and T directly, rather than their relative positions $R_A$, $R_P$, and $R_T$, since, for conceptual purposes, the distinction there between is of no significance to any of our calculations.

Given points A, P, and T, the navigation system calculates a line, M, between points A and P. Line M is roughly the femoral mechanical axis and its length is roughly the length of the femur. The navigation system then calculates another line, O, that is perpendicular to line M and that runs between line M and point T.

At this point, the navigation system has the following information: (1) the position of the anterior pelvic plane 202; (2) the position of the center of rotation of the native hip joint, A (which, by definition, is the center of rotation of the acetabulum and the center of rotation of the femoral head); (3) the position of the patella, P; (4) the position of the point on the greater trochanter, T; (5) the position and length of the femoral mechanical axis, M; and (6) the femoral offset distance, O.

if additional femoral landmarks were acquired, other distances and angles also can be calculated.

Next, the surgeon reams the acetabulum and implants the cup. More specifically, the surgeon chooses a reamer with an appropriate head reaming diameter and mounts a marker to it so that it can be tracked by the surgical navigation system. The reamer head is essentially a section of a sphere. As is known in the art, the reamer position at the end of the reaming process essentially defines the position that the prosthetic cup will have when it is implanted in the reamed acetabulum. The orientation of the reamer head also largely dictates the orientation (e.g., inclination and anteversion) that the prosthetic cup will have when it is implanted in the reamed acetabulum. However, there is a limited ability to change the final orientation of the cup within the reamed acetabulum during the implantation phase. Accordingly, the navigation system can be programmed to display to the surgeon during the reaming operation relevant information for properly orienting the cup. More specifically, it can show the x, y, z position of the center of rotation of the sphere defined by the reamer head.

The navigation system preferably also shows the inclination and anteversion angles of the reamer. At the end of the reaming operation, with the reamer held in its final reaming position, the surgeon causes the navigation system to record the position and orientation of the reamer, which, in turn, will dictate the position of the prosthetic cup and substantially dictate the orientation of the cup.

Next, the surgeon selects a suitable cup and attaches an impacter to the cup for hammering the cup into the reamed acetabulum. Since the cup orientation can be varied slightly within the reamed acetabulum during implantation, it is preferable to attach a marker to the cup (either directly or via the impacter) to track it also. The surgical navigation system is preprogrammed or otherwise with provided information as to the center of rotation and orientation of the cup relative to the impacter and/or marker. Since the coordinate position of the cup has already been dictated by the reaming operation and essentially cannot be affected at this point, the navigation system may display to the surgeon only the orientation of the cup in anteversion and inclination and not its position. Alternately, it may display its position in x, y, z coordinates.

Figure 5:
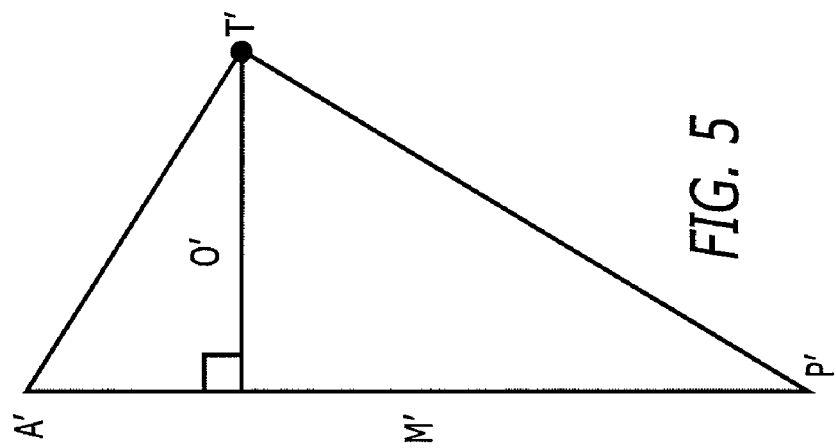
FIG. 5 is a drawing illustrating a second set of relevant landmarks and measurements in the pelvic frame of reference in accordance with an embodiment of the present invention.

With reference to FIG. 5, the center of rotation of the prosthetic cup in the pelvic frame of reference is shown at A'. As before with respect to FIG. 4, A' is not an absolute position, but is only known relative to the position of the pelvic marker. In one preferred embodiment of the invention, while the navigation system records A', it does not display it to the surgeon at this time. The navigation system also records the change in position between A and A' in terms of at least $\Delta y$ and $\Delta z$ values.

Next, the surgeon creates a hole or channel for accepting the stem of the femoral implant using a suitable surgical tool. Conventionally, surgeons typically use a rasp. However, it could also be a reamer or a drill. In any event, a marker is mounted to the tool and tracked by the system. The system is programmed with information as to the position of the operable portion of the rasp relative to the marker mounted on it. It also is programmed or otherwise provided with information as to the dimensions of the femoral implant so that it can calculate the position of the center of rotation of the prosthetic femoral head if implanted in the currently rasped channel as a function of the tracked position and orientation of the rasp. The navigation system, therefore, can be programmed to show the surgeon such information. This information can be shown to the surgeon in order to assist in the navigation of the rasp during rasping.

When the surgeon has created the channel inside the bone to a depth and in an orientation that he or she believes might be the final depth and orientation for implanting the femoral component, the surgeon leaves the tracked rasp in the bone and re-palpates the point or points previously palpated on the femur, e.g., the point on the patella and/or the point on the greater trochanter, and causes the navigation system to record these points again. With reference to FIG. 5, these points are shown as P' and T'.

In an alternative embodiment of the invention, the center of rotation of the femoral head can be determined by providing a rasp having a handle portion separable from the rasp operable portion and also providing a trial femoral head that can be placed on the proximal end of the rasp operable portion. Then, after rasping the channel to the desired depth and orientation, the surgeon could remove the rasp handle and replace it with the trial femoral head and then reassemble the joint. With the joint intact, the location of the center of rotation of the new femoral head, A', is fixed with respect to the pelvic marker and can therefore be tracked in the pelvic frame of reference. Then the surgeon could re-palpate the other points, P' and T', with the joint assembled. This embodiment has the advantage of permitting the navigation system to track and record the new points, A', P', and T' directly in the pelvic frame of reference.

Now having values for A', P', and T', the navigation system can calculate a new mechanical axis of the femur, M', as the line between A' and P' and the new femoral offset, O', as the perpendicular line between M' and T'.

The system then calculates a value $\Delta M$ as the difference in length between M and M' and a value $\Delta O$ as the difference in length between O and O'.

Furthermore, having calculated $\Delta M$, $\Delta O$, $\Delta y$, and $\Delta z$, the system has all the information it needs to calculate leg lengthening/shortening as well as medialization/lateralization for the given position of the implanted cup and the calculated position of the femoral prosthesis component. Specifically, the change in leg length is given by the sum of $\Delta M$ and $\Delta z$. The medialization/lateralization change is given by the sum of $\Delta O$ and $\Delta y$. Note that $\Delta y$ is a measurement in the medial/lateral frontal plane, whereas $\Delta O$ is not (typically, it is along the direction of the femoral neck, which usually is at an angle of about 15° to the frontal plane). Hence the change in medialization/lateralization caused by $\Delta O$ is more accurately given by the projection of the offset into the frontal plane would give the true medialization or lateralization. A correction for this can be made, such as by multiplying $\Delta O$ by the cosine of 15°, but the difference is likely to be negligibly small and, in a preferred embodiment of the invention, no such correction is made.

The navigation system shows these values to the surgeon so that the surgeon can determine whether he has rasped the channel for the femoral stem prosthesis appropriately (the surgeon, presumably, having previously determined desired leg length and medialization/lateralization values for the surgery). If not, the surgeon can rasp it further or take other steps to alter these values until he or she obtains the desired values for leg length and medialization/lateralization.

The invention is contemplated for use in connection with modular femoral implants comprising at least two components forming the stem of the implant, a first component designed to be implanted within the channel created in the femur and a second component to be coupled thereto and protrude outwardly of the femur. A prosthetic set, for instance, may comprise a single first stem portion and a plurality of second stem portions having different lengths, shapes and/or angles so that the surgeon could also adjust the leg length and medialization/lateralization by appropriate selection of the second stem component. A femoral head would be mounted on the end of the second stem portion. The prosthesis set may also comprise a plurality of different diameter femoral heads for different sized patients that also would affect the position of the center of rotation of the femoral head relative to the femur.

In a preferred embodiment of the invention, the navigation system is preprogrammed or otherwise provided with information as to the dimensions of all of the potential second stem components and/or femoral head components and can display to the surgeon the leg length and medialization/lateralization for all options to assist the surgeon in choosing the most appropriate second stem portion and/or femoral head.

The software for providing the functionality of the present invention as described above can preloaded on the memory of the computer of the navigation system or can be provided on a separate computer readable medium from which it can be loaded onto the computer of the navigation system.

Figure 6:
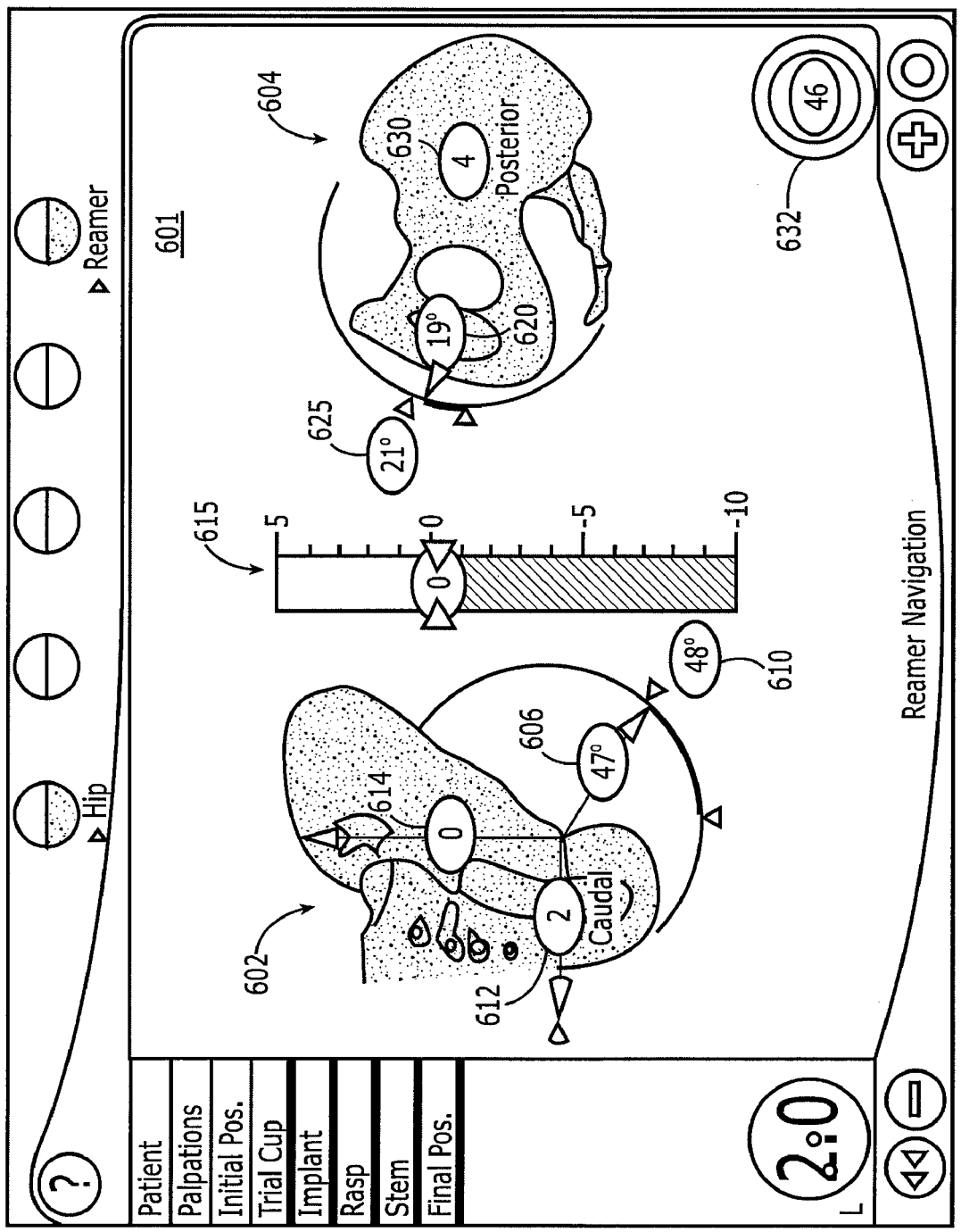
FIG. 6 is an exemplary display generated by a surgical navigation system during a first stage of an exemplary hip replacement surgery in accordance with the present invention.
Figure 7:
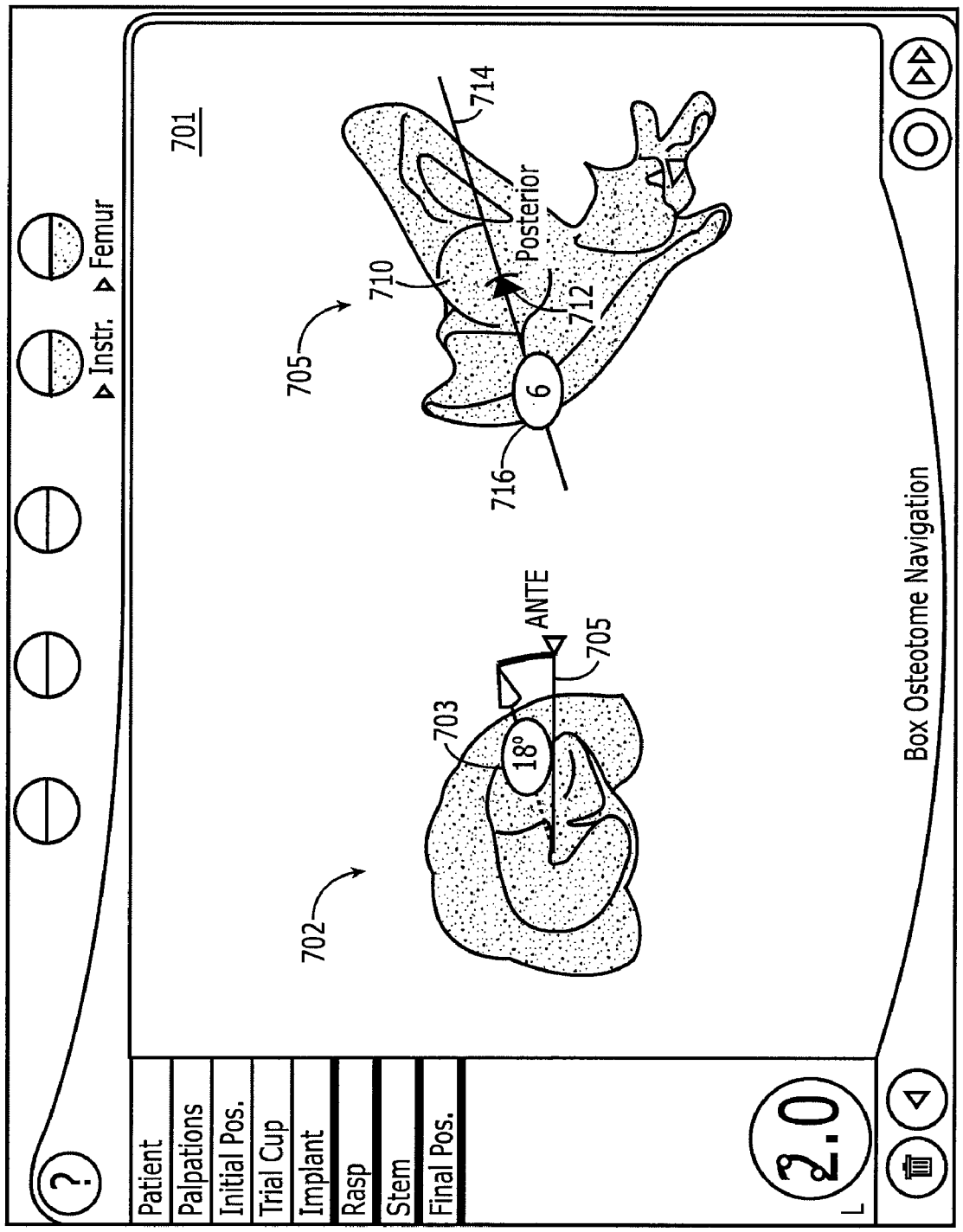
FIG. 7 is an exemplary display generated by a surgical navigation system during a second stage of an exemplary hip replacement surgery in accordance with the present invention.

The navigation system can display to the surgeon all of the information discussed hereinabove in any reasonable manner. FIGS. 6 and 7 are screen shots of exemplary display formats for different stages of the procedure. However, these are merely exemplary and many other display modes are possible.

FIG. 6, for instance, illustrates an exemplary display 601 that can be displayed on the monitor of the surgical navigation system when the surgeon is reaming the acetabulum for accepting the cup. A very similar display also may be used during the actual cup implantation. The monitor displays a frontal view 602 of the pelvis on the left and a lateral view 604 on the right. In the frontal view 602, the display shows the inclination angle of the cup at 606. Further, in a preferred embodiment of the invention, the surgeon can input into the system the inclination angle of the native acetabulum and the display can simultaneously show this value for the surgeon's reference, such as shown at 610. In addition, ovals 612 and 614, respectively, show the y and z positions of the cup in millimeters. In a preferred embodiment of the invention, these values are shown as the changes from the original y and z position of the center of rotation of the pre-surgical acetabulum. The display also shows the reamer depth both numerically and graphically at 615 in the middle of the display. The displayed reamer depth value is the minimum distance between the aforementioned reference point on the native acetabulum previously palpated by the surgeon and the surface of the reamer. In the frontal view 602 shown on the left of the screen, the display shows the inclination angle of the cup numerically at 606. In addition, in a preferred embodiment of the invention, the system also displays the inclination angle of the native acetabulum at 625 as previously determined for purposes of reference. The right hand portion of the display also shows, at 630, the position of the cup in the X direction (again displayed as an offset from the original X position of the center of rotation of the pre-surgical acetabulum). The display shows the anteversion angle at 620 in the lateral view 604. Finally, the diameter of the reamer (or cup) selected by the surgeon is shown at 632 in the lower right hand corner of the display. The surgeon having input such information into the system at an appropriate earlier stage of the procedure. The reamer diameter or cup diameter is displayed at 632 in the lower right-hand corner.

In a preferred embodiment of the invention, the y and z positions 612, 614 and the depth of the cup are shown only during reamer navigation and not during cup navigation since those values cannot be changed during cup navigation. Only the inclination and anteversion angles are changeable during cup implantation.

FIG. 7 shows an exemplary display 701 during rasp navigation. The left-hand illustration 702 shows the femur with its head resected. The displayed angle 703 represents the anteversion angle. The reference line 705 for this angle runs parallel to the dorsal condyle line. The right hand illustration 706 shows the view from the cranial direction of the pelvis and the implanted cup 710. The cup is displayed transparently. The point 712 at the center of the cup represents the center of rotation of the cup. The orientation of the instrument plane is displayed with reference to the center of rotation at 714. The value displayed in oval 716 is the distance between this point and the instrument plane in millimeters in the anterior/posterior direction. If this value is zero, the instrument plane runs exactly through the new center of rotation.

Figure 8:
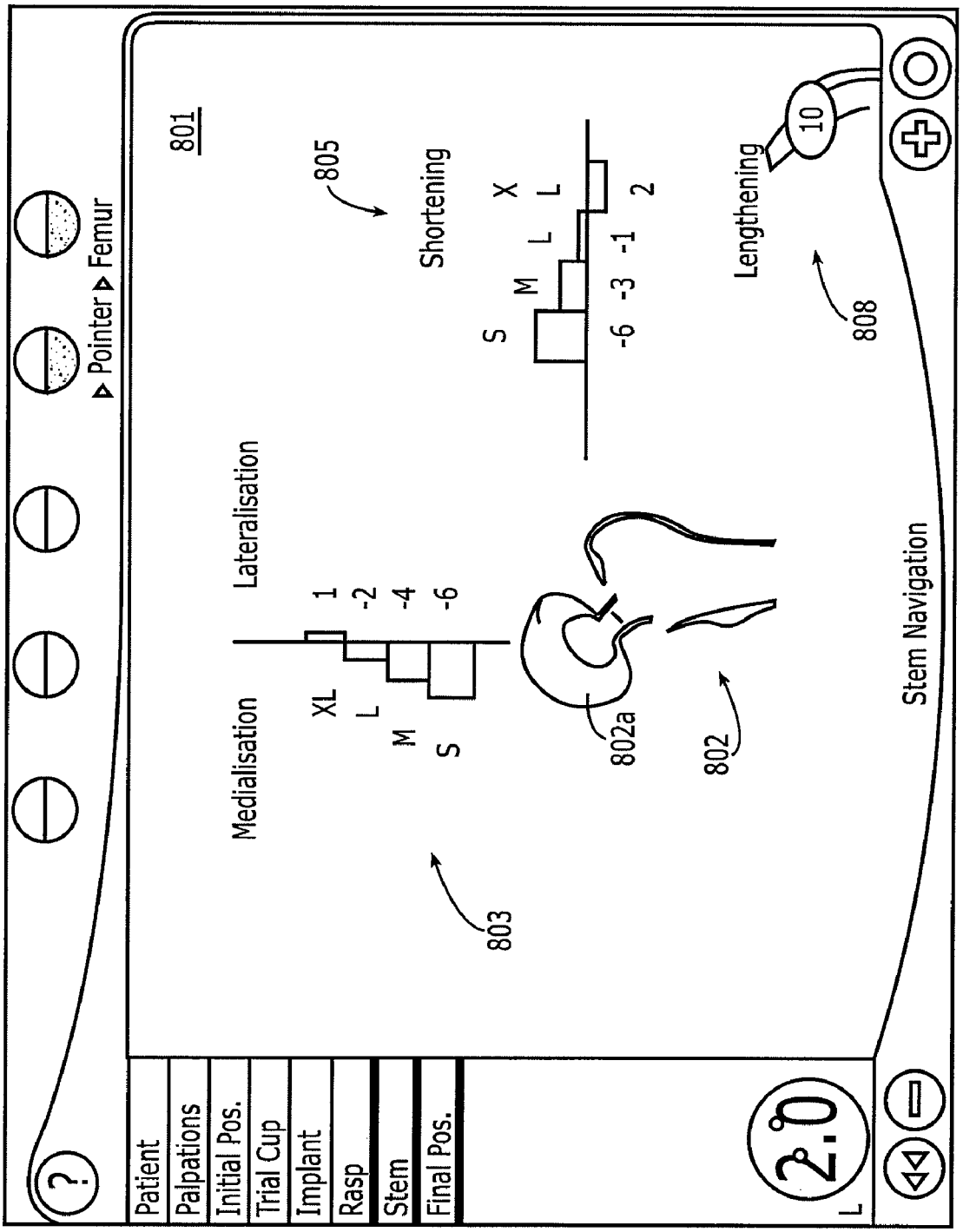
FIG. 8 is an exemplary display generated by a surgical navigation system during a third stage of an exemplary hip replacement surgery in accordance with the present invention.

FIG. 8 illustrates an exemplary display 801 for the femoral stem navigation stage of the procedure. In this example, the stem is not modular and there are four different femoral head sizes that can be attached to the end of the stem, termed S for small, M for medium, L for large, and XL for extra large. The display includes a pictorial representation 802 of the femur with the prosthesis 802a implanted (including a representational head). Portion 803 graphically and numerically illustrates the medialization/lateralization that would result from installation of each of the four heads. Portion 805 represents the leg lengthening/shortening that would result from each of the four heads. The numbers are in millimeters and represent the change from the original, pre-surgical positions.

Figure 9:
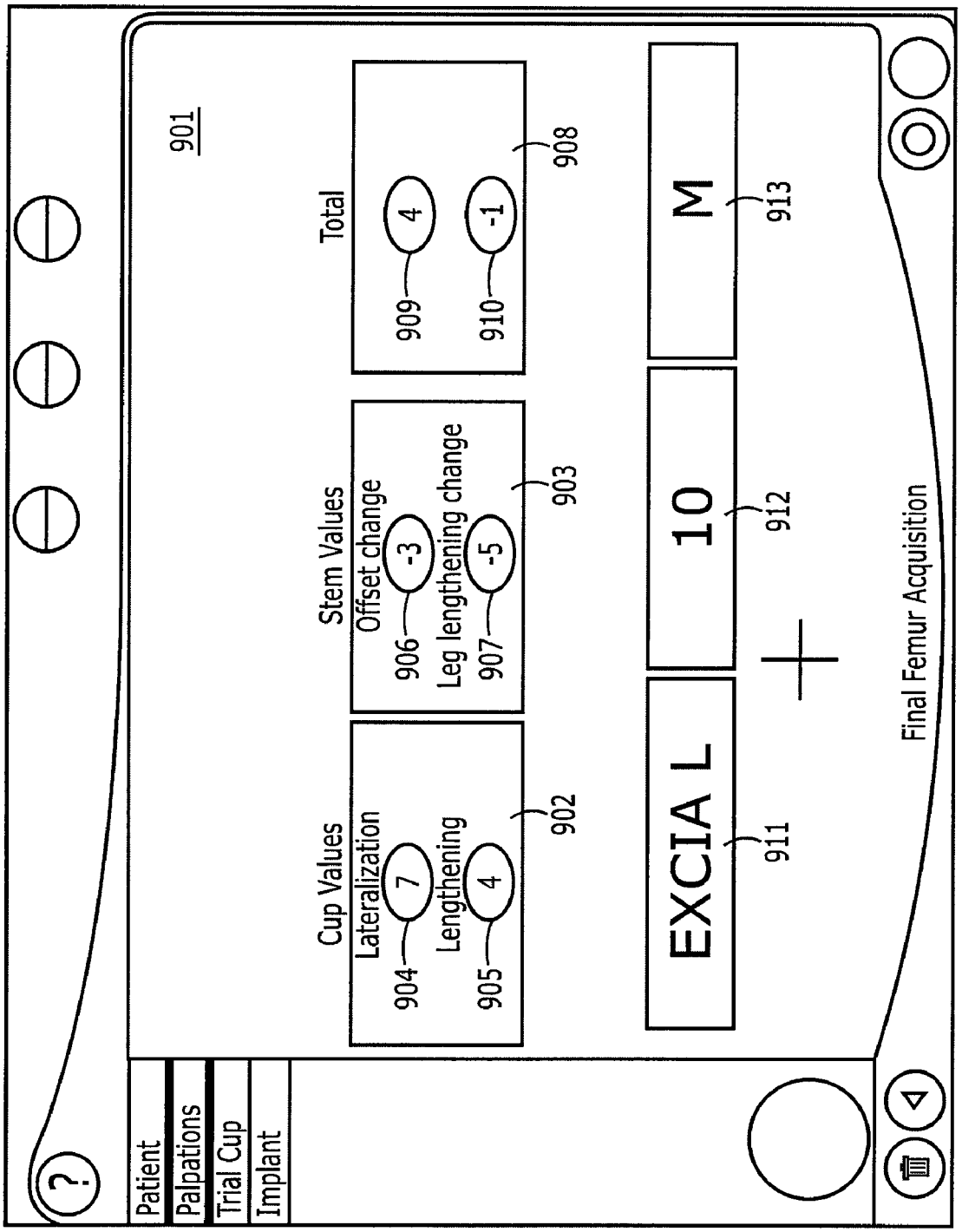
FIG. 9 is an alternative display generated by a surgical navigation system during a third stage of an exemplary hip replacement surgery in accordance with the present invention.

When the navigation system is used in connection with a prosthesis set having modular stems, the display can be adapted to generate a separate display similar to that shown in FIG. 8 for each potential stem. Alternately, a strictly numerical display such as shown in FIG. 9 can be generated. In this display 901, for instance, the particular implant series is shown in box 911, the length of the particular stem is shown in box 912 and the size of the particular head is shown in box 913. The left hand box 902 shows the medialization/lateralization change information and the leg lengthening/shortening change information resulting from the cup implantation in the pelvis while the middle box 903 shows similar information resulting from the femoral implant component. Specifically, oval 904 shows the medialization/lateralization change resulting from the cup implanted in the pelvis and oval 905 shows the leg lengthening/shortening change resulting from the cup. In the middle box, 903, oval 906 shows the femoral offset change data resulting from the femoral implant component and oval 907 shows the leg lengthening/shortening data resulting from the femoral implant component.

The right-hand box 908 shows the total for medialization/lateralization in oval 909 and the total for leg lengthening/shortening in oval 910. The total for medialization/lateralization in oval 909 is the sum of the values in ovals 904 and 906. The total for leg lengthening shown in oval 910 is the sum of the values in ovals 905 and 907. The surgeon can scroll through these displays, each display showing the leg lengthening/shortening results and medialization/lateralization results for a different permutation of the available femoral head and stem components in a given set as well as different sets.

Once the surgeon has selected a second stem component and/or femoral head size, the marker can be removed from the first, implanted stem portion and the modular stem portion and/.or femoral head can be installed. The surgery can then be completed in the conventional manner by fitting the femoral head in the cup and closing the incision.

Preferably, the navigation system is pre-programmed or otherwise provided with the relevant dimensions of the prosthetic components that can be implanted using the navigation system. The software can be pre-programmed with such information for a number of different implant sets and presents the surgeon at some point before or during the surgery with a display that permits the surgeon to choose the implant set he or she intends to use for the surgery.

It also should be possible to calculate and display to the surgeon the range of motion of the femur relative to the pelvis. It may require the palpation of some additional points on the femur and/or pelvis in order to determine range of motion values.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of using a surgical navigation system for positioning in a femur a femoral prosthetic component of a hip joint replacement prosthesis, said method comprising the steps of:

acquiring a pelvic frame of reference;

acquiring a center of rotation of said hip joint in said pelvic frame of reference;

acquiring a first femoral point substantially fixed with respect to said femur in said pelvic frame of reference while said hip joint is intact;

calculating a length of a first line between said first acquired femoral point and said center of rotation of said hip joint;

implanting a prosthetic cup component of said hip joint replacement prosthesis in said pelvis;

acquiring a position of a center of rotation of said implanted prosthetic cup component in said pelvic frame of reference;

calculating a first difference in position between said center of rotation of said hip joint and said center of rotation of said implanted prosthetic cup component in said pelvic frame of reference;

forming a hole in said femur for accepting said femoral prosthetic component;

rigidly mounting a marker in said hole, said marker having a known position relative to a position of a center of rotation of a prosthetic femoral head of a femoral prosthetic component if implanted in said hole;

calculating a position of a center of rotation of said prosthetic femoral head if implanted in said hole as a function of said position of said marker mounted in said hole;

while said marker is mounted in said hole, re-acquiring said first femoral point relative to said position of said marker mounted in said hole;

calculating a length of a second line between said re-acquired first femoral point and said center of rotation of said prosthetic femoral head;

calculating a second difference in length of said first line and said second line; and displaying leg length data as a function of said first and second differences.

2. The method of claim 1 wherein said first difference is a difference in position within a caudal-cranial direction and wherein said function of said first and second differences comprises a first sum of said first and second differences.

3. The method of claim 2 wherein said displayed leg length data is said sum.

4. The method of claim 1 wherein said displaying step comprises displaying a plurality of potential leg lengths corresponding to a plurality of different potential femoral prosthetic implants that can be implanted in said hole.

5. The method of claim 1 wherein said femoral prosthetic implant is modular and wherein said displaying step comprises displaying a plurality of potential leg lengths corresponding to a plurality of different potential modular femoral prosthetic implant components that can form said femoral prosthetic implant.

6. The method of claim 1 further comprising the steps of:

while said femur is in a same position as it was when said first femoral point was acquired, acquiring a second femoral point not on said first line;

calculating a length of a third line perpendicular to said first line between said first line and said acquired second femoral point;

while said marker is mounted in said hole, re-acquiring said second femoral point relative to said position of said marker mounted in said hole;

calculating a length of a fourth line perpendicular to said second line between said second line and said re-acquired second femoral point;

calculating a third difference in length of said third line and said fourth line.

7. The method of claim 6 wherein said second femoral point is a point on a greater trochanter of said femur.

8. The method of claim 6 further comprising the step of:

calculating a fourth difference in position between said center of rotation of said hip joint and said center of rotation of said implanted prosthetic cup component in said pelvic frame of reference;

wherein said displaying step further comprises displaying a value for medialization/lateralization as a function of said third and fourth differences.

9. The method of claim 8 wherein said fourth difference is a difference in position within a medial-lateral direction and wherein said function of said third and fourth differences comprises a second sum of said third and fourth differences.

10. The method of claim 6 wherein said displayed value for medialization/lateralization is said second sum.

11. The method of claim 6 wherein said displaying step comprises displaying a plurality of potential values for medialization/lateralization corresponding to a plurality of different potential femoral prosthetic implants that can be implanted in said hole.

12. The method of claim 6 wherein said femoral prosthetic component is modular and wherein said displaying step comprises displaying a plurality of potential values for medialization/lateralization corresponding to a plurality of different potential modular femoral prosthetic implant components that can form said femoral prosthetic implant.

13. The method of claim 6 wherein said second femoral point is a point on a greater trochanter of said femur.

14. The method of claim 6 wherein said first and second femoral points are acquired simultaneously.

15. The method of claim 6 wherein said first and second femoral points are recorded sequentially and wherein said femur is not substantially moved between said acquiring of said first femoral point and said acquiring of said second femoral point.

16. The method of claim 1 further comprising the step of:

visibly marking said first point prior to said re-acquiring step.

17. The method of claim 1 wherein said step of forming a hole comprises tracking with said surgical navigation system a tool that forms said hole and displaying a position and orientation of said tool during said forming.

18. The method of claim 17 wherein said rigidly mounting step comprises mounting said marker to said tool and disposing said tool in said hole.

19. The method of claim 1 wherein said first femoral point is approximately on a mechanical axis of said femur.

20. The method of claim 19 wherein said first femoral point is a point on a patella.

21. The method of claim 20 wherein said step of acquiring said first femoral point comprises palpating said patella over the skin with a surgical pointer tracked by said surgical navigation system.

22. The method of claim 1 wherein said step of acquiring said pelvic frame of reference comprises acquiring the anterior pelvic plane.

23. The method of claim 1 wherein the step of acquiring said pelvic frame of reference comprises:
acquiring first, second, and third non-coaxial points on said pelvis; and
calculating a plane defined by said points.

24. The method of claim 23 wherein said step of acquiring said first, second, and third points on said pelvis comprises:
fixedly mounting a first marker trackable by said surgical navigation system to said pelvis, said marker defining to said surgical navigation system said pelvic frame of reference;
fixedly mounting a second marker trackable by said surgical navigation system to a surgical pointer;
palpating said first, second, and third points with said surgical pointer while said surgical navigation system records the positions of said first, second, and third points relative to said first marker; and
calculating said anterior pelvic plane in said pelvic frame of reference.

25. The method of claim 1 wherein said steps of acquiring and re-acquiring said first femoral point comprise:
palpating said first femoral point with a surgical pointer tracked by said surgical navigation system.

26. The method of 1 wherein a leg of said patient is maintained in about the same amount of flexure during performance of said method.

27. The method of claim 1 wherein said step of acquiring a center of rotation of said hip joint in said pelvic frame of reference comprises;
placing a cup trackable by said surgical navigation system in said acetabulum such that the cup mimics the center of rotation of the acetabulum; and
determining a center of rotation of said cup in said pelvic frame of reference.

28. The method of claim 1 wherein said step of acquiring a center of rotation of said hip joint in said pelvic frame of reference comprises;
palpating a plurality of points on said acetabulum while said surgical navigation system records the positions of each of said plurality of points relative to said first marker;
calculating a center of a sphere that is best defined by said plurality of points.

29. A computer readable product embodied on computer readable media readable by a computing device for generating a display for a surgical navigation system to be used for positioning in a femur a femoral prosthetic component of a hip joint replacement prosthesis, the product comprising:
first computer executable instructions for acquiring a pelvic frame of reference;
second computer executable instructions for acquiring a center of rotation of said hip joint in said pelvic frame of reference;
third computer executable instructions for acquiring a first femoral point substantially fixed with respect to said femur in said pelvic frame of reference;
fourth computer executable instructions for calculating a length of a first line between said first acquired femoral point and said center of rotation of said hip joint;
fifth computer executable instructions for acquiring a position of a center of rotation of said implanted prosthetic cup component in said pelvic frame of reference;
sixth computer executable instructions for calculating a first difference in position between said center of rotation of said hip joint and said center of rotation of said implanted prosthetic cup component;
seventh computer executable instructions for calculating a position of a center of rotation of a prosthetic femoral head of a femoral prosthetic implant if implanted in said hole as a function of said position of said marker mounted in said hole;
eighth computer executable instructions for re-acquiring said first femoral point relative to said position of said marker mounted in said hole while said marker is mounted in said hole;
ninth computer executable instructions for calculating a length of a line between said re-acquired first femoral point and said center of rotation of said prosthetic femoral head;
tenth computer executable instructions for calculating a second difference in length of said first line and said second line; and
eleventh computer executable instructions for displaying leg length data as a function of said first and second differences.

30. The product of claim 29 wherein said first difference is a difference in position within a caudal-cranial direction and wherein said function of said first and second differences comprises a first sum of said first and second differences.

31. The product of claim 29 wherein said eleventh computer executable instructions comprise instructions for displaying a plurality of potential leg lengths corresponding to a plurality of different potential femoral prosthetic implants that can be implanted in said hole.

32. The product of claim 29 further comprising:
twelfth computer executable instructions for acquiring a second femoral point not on said first line while said femur is in a same position as it was when said first femoral point was acquired;
thirteenth computer executable instructions for calculating a length of a third line perpendicular to said first line between said first line and said acquired second femoral point;
fourteenth computer executable instructions for re-acquiring said second femoral point relative to said position of said marker mounted in said hole while said marker is mounted in said hole;
fifteenth computer executable instructions for calculating a length of a fourth line perpendicular to said second line between said second line and said re-acquired second femoral point; and
sixteenth computer executable instructions for calculating a third difference in length of said third line and said fourth line.

33. The product of claim 32 further comprising:
seventeenth computer executable instructions for calculating a fourth difference in position between said center of rotation of said hip joint and said center of rotation of said implanted prosthetic cup component;

wherein said eleventh computer executable instructions comprise instructions for displaying a value for medialization/lateralization as a function of said third and fourth differences.

34. The product of claim 33 wherein said fourth difference is a difference in position within a medial-lateral direction and wherein said function of said third and fourth differences comprises a second sum of said third and fourth differences.

35. The product of claim 29 wherein said first femoral point is approximately on a mechanical axis of said femur.

36. The product of claim 35 wherein said first femoral point is a point on a patella and wherein said step of acquiring said first femoral point comprises palpating said patella over the skin with a surgical pointer tracked by said surgical navigation system.

37. The product of claim 29 wherein said fifth computer executable instructions comprise;
- instructions for acquiring at least one point on said pelvis from which said center of rotation of said hip joint can be determined;
- instructions for calculating said center of rotation of said hip joint based on said point on said pelvis.

* * * * *